United States Patent [19]

Halmann et al.

[11] Patent Number: 5,151,856
[45] Date of Patent: Sep. 29, 1992

[54] METHOD OF DISPLAYING CORONARY FUNCTION

[75] Inventors: Menachem Halmann; Haim Azhari; Rafael Beyar; Samuel Sideman; Uri Dinnar, all of Haifa, Israel

[73] Assignee: Technion R & D Found. Ltd., Haifa, Israel

[21] Appl. No.: 400,689

[22] Filed: Aug. 30, 1989

[51] Int. Cl.⁵ .............................................. G06F 15/00
[52] U.S. Cl. ........................... 364/413.03; 364/413.02; 364/413.13
[58] Field of Search ...................... 364/413.06, 413.03, 364/413.13, 413.14, 413.02; 128/731

[56] References Cited

U.S. PATENT DOCUMENTS

| 4,898,181 | 2/1990 | Kessler | 128/710 |
| 4,949,725 | 8/1990 | Raviv et al. | 128/731 |
| 4,974,598 | 12/1990 | John | 364/413.06 |

OTHER PUBLICATIONS

Samuel Sideman et al., "Three-Dimensional Computer Simulation of the Cardiac System" Proceedings of the IEEE, vol. 76, No. 6, Jun. 1988.
Haim Azhari et al., "Quantitative Characterization and Sorting of Three-Dimensional Geometrics: Application to Left Ventricles In Vivo", IEEE Transactions in Biomedical Engineering, vol. 36, No. 3, Mar. 1989.
S. Eiho, N. Matsumoto, M. Kuahara, T. Matsuda and C. Kawai, "3-D Reconstruction and Display of Moving Heart Shapes from MRI Data," IEEE Computers in Cardiology pp. 349-352; 1988.
Akima, H., "A New Method of Interpolation and Smooth Curve Fitting Based on Local Procedures," Journal of the Association for Computing Machinery, vol. 17, pp. 589-602, Oct. 1970.
H. Azhari, R. Beyar, E. Barta, U. Dinnar and S. Sideman, "A Combined Computer Simulation of Left Ventricular Dynamics," Proc. of the 4th Mediterranean Conference on Medical and Biomedical Eng., Sevilla, Spain, pp. 189-193, 1986.
Azhari H., Sideman S., Beyar R., Granadier E., Dinnar U.: *An analytical shape descriptor of 3-D geometry. Application to the analysis of the left ventricle shape and contraction,* IEE Trans. on Biomed. Eng. 34(5): 345-355, 1987.

Primary Examiner—Roy N. Envall, Jr.
Assistant Examiner—Laura Brutman
Attorney, Agent, or Firm—Herbert Dubno

[57] ABSTRACT

A method of displaying cardiac function which forms by helical or segmental analysis a three-dimensional cage model which can be shaded and color coded to indicate local and regional dysfunction by thickening or motion and stresses. On this model is superimposed the coronary artery tree including stenosed segments as obtained from the same patient by angiograms and the resulting three-dimensional coronary and mechanical model can be subjected to animation and analysis for diagnostic purposes and to simulate effects of treatment.

17 Claims, 1 Drawing Sheet

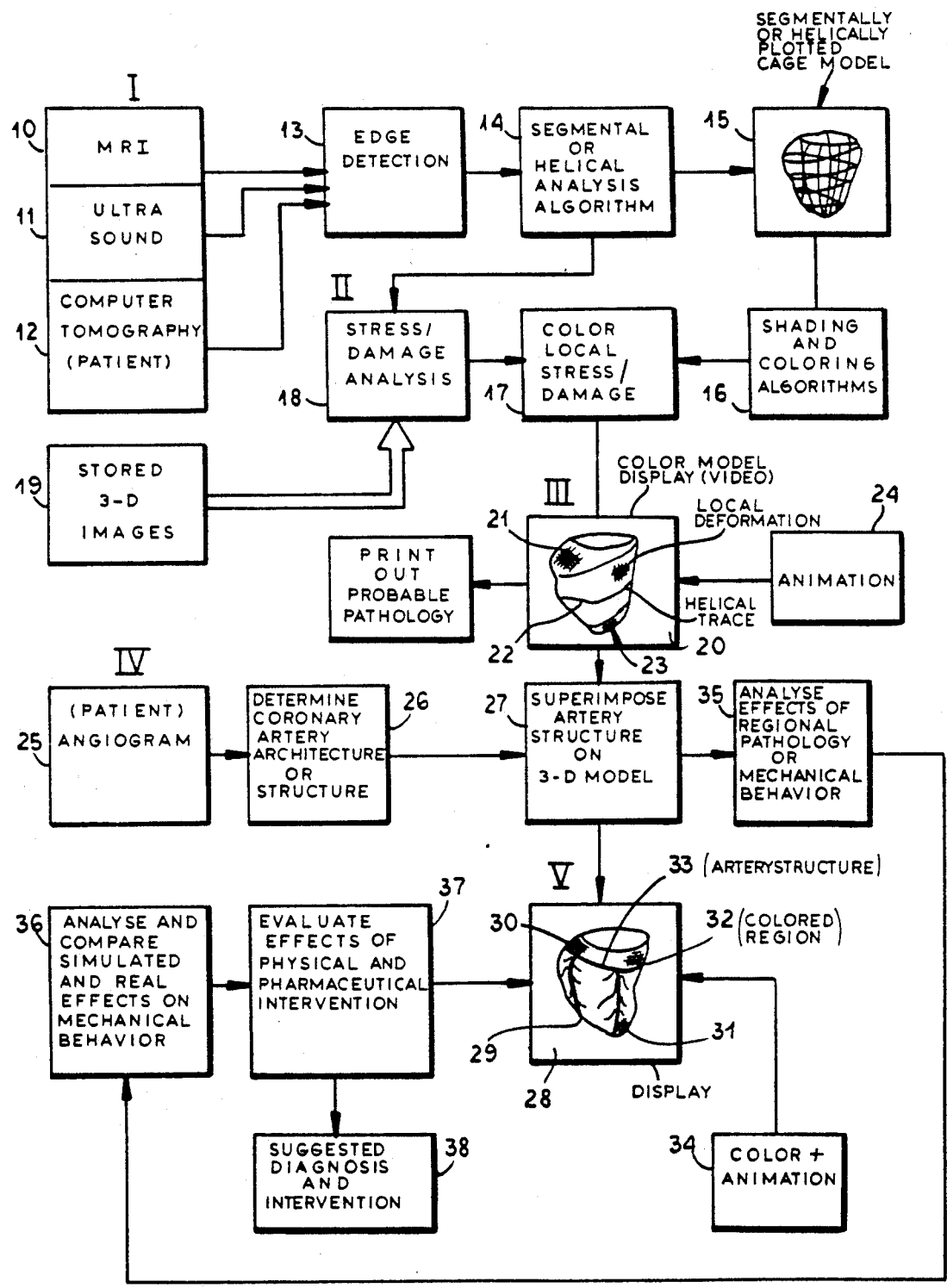

METHOD OF DISPLAYING CORONARY FUNCTION

FIELD OF THE INVENTION

Our present invention relates to a method of displaying coronary anatomy in 3D, superimposed and displayed on the heart of an animal subject, especially a human patient, to enhance diagnosis, study and treatment. Specifically the method displays the heart of a human patient with its coronary anatomy and its regional function color coded thereon on a computer screen.

BACKGROUND OF THE INVENTION

A variety of approaches to three-dimensional reconstruction, simulation and animation of heart models have been provided heretofore and, for example, an ultrasound image can be made of the human heart in vivo and can be displayed in a silhouette or shadow display. Heart models have been displayed heretofore in three dimensions and it has even been proposed to animate such models so that the functioning of the heart can be displayed for teaching, research or evaluation purposes. However, while a variety of methods of analyzing defects in the human heart have been developed, there has not been, to our knowledge, any method provided heretofore which will not only permit evaluation of defective regions of the human heart by three-dimensional reconstruction and visualization thereof, but can also relate structural defect regions to the individual coronary pattern, structure and possible pathology.

OBJECTS OF THE INVENTION

It is, therefore, the principal object of the present invention to provide a method for the three-dimensional reconstruction, simulation and animation of the heart which is additionally capable of analyzing and displaying regional myocardial function and/or pathology or defects.

Another object of this invention is to provide a method for the purposes described which enables a correlation of regional pathology or any pathological myocardial function with coronary artery anatomy (e.g. stenosis, obstruction), superimposed upon the reconstructed 3D heart.

It is also an object of the invention to provide a method of displaying a heart which can facilitate research into the functioning and pathologies of the heart, can facilitate diagnosis of specific pathologies for a specific patient, and can be used both as a research and teaching tool.

A highly important object of the invention is to relate, in a readily depictable manner, local coronary blood flow disturbances due to stenosis and obstructions to regional mechanical dysfunction of the heart. In addition, it will also be used to evaluate the outcome of progressive coronary pathology and to study the significance of coronary pathological lesions.

SUMMARY OF THE INVENTION

These objects and others which will become apparent hereinafter are attained, in accordance with the present invention, by a method of computerized analysis of noninvasively acquired heart scans, whether these are made by MRI, computer tomography in general or Cine-CT in particular, ultrasound or some other scanning technique, to enable the reconstruction in three dimensions of the heart thus scanned.

According to an essential feature of the invention, regional myocardial function is determined, e.g. by the scan, in terms of, for example wall thickening, wall thinning or wall motion, and those regions having regional myocardial functions deviating from normal function or from the corresponding function of an adjacent part, are displayed on the three-dimensional video model which can be rotated about any axis by regional color differences, thereby enabling the cardiologist, physician or patient to view directly areas of defective myocardial function or subject to other pathologies, or regions which may have suffered infarct or other ischemic changes.

According to an important feature of this invention, utilizing angiography, a video angiogram is made of the coronary artery structure of the patient and is superimposed, with proper scaling, and match to the three-dimensional display described previously, on the three-dimensional color display of the heart.

By using the patient's own angiogram superimposed on the reconstructed heart of that patient, a correlation can readily be made between coronary artery pathologies and adjacent myocardial dysfunction.

The coronary tree is superimposed simply by utilizing anatomical landmarks obtained in the normal angiography, which also characterizes the individual characteristics of the coronary tree.

In particular, the comparison of regions supplied by stenosed vessels with independently determined (thickening, motion, stress) mechanical function will yield four different combinations: (i) a normal, functioning zone with adequate coronaries; (ii) a zone of matched coronary deficiency with regional dysfunction; (iii) a zone of coronary stenosis but with normal mechanical function; (iv) a zone of normal coronaries but with mechanical dysfunction.

According to another feature of the invention, the three-dimensional display having locally colored regions representing regions of unusual myocardial function and the patient's own angiogram superimposed thereon can be subjected to animation, e.g. to show the beating heart. Naturally, the animation can be varied to show the effect of different loads and heart rates (normal, tachycardia or bradycardia) or a normal heart rate. The animation can include, if desired, results of simulation of effects of components representing the subjection of the heart to various loadings, positive or negative inotropic influence (i.e. a greater or a lesser contractile force), and pathological conditions.

Advantageously, the three-dimensional dynamic imaging of the heart utilizing the image acquisition techniques of MRI and Cine-CT, for example, can be reconstructed and subjected to an analysis algorithm with an anatomically aligned helical system in which a cage model is first formed and then transformed by solid shading to the final three-dimensional model.

The latter approach for magnetic resonance imaging has been described by R. Beyar, E. Shapiro, W. Rogers, R. Solen, J. Weiss, and M. L. Weisfeldt, in "Accuracy of LV Thickening Using Three Dimensional Magnetic Resonance Imaging Reconstruction," 60th Scientific Session, AHA, Anaheim, November 1987, see also Quantitative Characterization and Sorting of Three-Dimensional Geometries: Application to Left Ventricles In Vivo, AZHARI, H. et al, IEEE Transactions on Biomedical Engineering 36, #3, P. 322 ff; March 1989.

The coronary tree can be superimposed on the epicardial surface utilizing the anatomical markers of the latter such as the anterior and posterior interventricular grooves or ventriculo-atrial grooves. The location of stenosed vessels can be displayed directly or emphasized in regional coloration and regional ischemic conditions can be simulated as well.

We have found that it is possible, by analyzing the MRI or Cine-CT "slices" to determine abnormalities of function by the shape analysis and to emphasize these regions by appropriate coloration of the three-dimensional models. The dysfunction can be in terms of deformation, wall motion, wall thickness and regional stress. The entire process is, of course, noninvasive and capable of providing a display of regional and global dysfunction in terms of appropriate coloration.

It is also possible, utilizing the display as obtained to predict where stenosed vessels might be located where such stenoses are not readily apparent from the coronary tree display on the model by determining regional dysfunctions of the myocardium.

All of the computer graphic facilities currently available can be brought to bear on the model obtained, i.e. the model can be dissected to view the endocardial surface, rotated to any position, etc.

More specifically, the method of the invention can be considered to comprise the steps of:

(a) utilizing an imaging device generating a plurality of two-dimensional sections of a mammalian heart;

(b) subjecting said sections to manual or automatic edge detection by computer aided tracing of borders;

(c) subjecting the resulting sections to a segmental or helical pattern analysis to generate a three-dimensional model of said mammalian heart;

(d) subjecting said mammalian heart to angiography to obtain the coronary artery pattern of said mammalian heart;

(e) superimposing said coronary artery pattern on said three-dimensional model using as a reference for locating said coronary artery pattern relative to said model a structural element of said mammalian heart detected in said model; and (f) displaying said model with said artery pattern superimposed thereon in a three-dimensional display.

As noted, images of the two-dimensional sections of the mammalian heart are generated in step (a), preferably by magnetic resonance imaging, computer tomography or ultrasound.

The displayed model with the artery pattern superimposed thereon can be subjected to animation representing a beating of the heart depicted by the model which is displayed on a color video monitor.

The method of the invention can, moreover, comprise the steps of storing three-dimensional models or data in analytic or compressed form representing a normal heart and hearts with various pathologies, electronically comparing the displayed model with the stored three-dimensional models or data and automatically indicating a pathological state of the mammalian heart by the comparison.

The stored three-dimensional models can include models of hearts with coronary diseases including ischemic heart disease and infarcts, aneurism, hypertrophy, cardiomyopathy and valvular diseases.

In accordance with another aspect of the invention a method of displaying mechanical function of a mammalian heart can comprise the steps of:

(a) electronically generating a plurality of two-dimensional sections of a mammalian heart;

(b) subjecting said sections automatically to a segmental or helical pattern analysis to generate a three-dimensional model of said mammalian heart;

(c) analyzing said sections for ascertaining a presence of mechanical degradation of certain zones of the heart;

(d) electronically coloring zones of the displayed model corresponding to said certain regions;

(e) displaying said model with said colored zones; and (f) subjecting the model displayed in step (e) to video animation.

BRIEF DESCRIPTION OF THE DRAWING

The above and other objects, features and advantages of the present invention will become more readily apparent from the following description, reference being made to the accompanying drawing, the sole FIGURE of which is a block diagram illustrating the method of the invention.

SPECIFIC DESCRIPTION

As has been illustrated in block diagram form in the drawing, the method of the invention comprises as a first step I the obtaining of two-dimensional sections of the heart of a patient by one of the conventional techniques currently in use to image the heart and heart function. In stage I for example, the heart sections of the patient can derive from MRI 10, ultrasonic imaging 11 or computer tomography 12, especially Cine-CT.

The obtaining of data in this fashion is described, inter alia in S. Eiho, N. Matsumoto, M. Kuahara, T. Matsuda and C. Kawai, "3-D Reconstruction and Display of Moving Heart Shapes from MRI Data," IEEE Computers in Cardiology, pp. 349-352; 1988.

More particularly, as described by EIHO et al: "The steps for 3-D reconstruction of left- and right-ventrical and both atrium of the heart are as follows:

Step 1: Pick up 3 sets of 2 image planes from each transverse (across Z-axis), coronal (Y-axis) and sagittal (X-axis) images.

Step 2: Draw the boundary curves of the organ on these images by using a track ball.

Step 3: Reconstruct 3-D shapes in a 32×32×32 voxel space. 3-D voxel reconstruction is executed automatically by the following steps.

Step 3.1: Draw boundary curves in the voxel space. If we look at a plane perpendicular to a coordinate axis, we can find 8 points at which 4 boundary curves intersect on that plane.

Step 3.2: Connect these points with spline curves and fill the inner part of the boundary. Thus we get several cross sectional shapes of the left ventricle on every Y-plane in this example.

Step 3.3: Execute the same procedure to X and Z planes.

Step 3.4: Smooth these X-, Y- and Z-plane 3-D shapes in their 3-D spaces (size for smoothing in 3×3×3), sum up in one 3-D voxel space and cut by a threshold value. Thus we can get 3-D voxel shape of the organ.

The sorts and pulmonary artery are reconstructed as a kind of circular tubes: By drawing the center line of the artery on a coronal and a sagittal images and by fixing radii on several points along the line, 3-D shapes of the arteries in the voxel spaces are obtained by interpolating the radius of the artery of each 2-cross sectional plane.

The two-dimensional images which are thus obtained can be subjected to an edge detection algorithm as represented at 13 to serve as a basis for segmental or helical analysis 14 of the sections and reconstruction of a three-dimensional cage model 15 therefrom (see H. Azhari, R. Beyar, E. Barta, U. Dinnar and S. Sideman, "A Combined Computer Simulation of Left Ventricular Dynamics," Proc. of the 4th Mediterranean Conference on Medical and Biological Eng., Sevilla, Spain, pp. 189-193, 1986). This reconstruction can proceed based upon the following: "If we consider an imaginary cylinder which surrounds the LV, with a diameter (D) larger than the largest diameter of the LV and which axis is parallel to the major axis of the LV, as shown in FIG. 1. By moving along a helical curve, located on the surface of the cylinder, and measuring the external radial distance (R) from the helix to the endocardial surface, a unidimensional function, $R(\xi)$, is obtained. This function $R(\xi)$, which represents a helical curve wrapped around the endocardial surface can be used to approximate the 3-D geometry of the LV cavity. In order to retain the same helical representation for every element, the curvilineary coordinate $\xi$ is allowed to deform vertically (H becomes a function of $\xi$) along with the LV. Thus, the instantaneous geometry of the LV cavity ($(\xi, t)$) is defined by two functions:

$$(t,\xi) = \begin{cases} R(t,\xi) \\ H(t,\xi) \end{cases}$$

Given the two instantaneous principle deformations, for a given myocardial element, the corresponding functions $R(t+dt,\xi)$, and $M(t+dt, \xi)$ can be estimated, using the following kinematic assumptions.

The first assumption is that all endocardial points on a cross section perpendicular to the major axis deform radially with reference to the instantaneous centroid of this cross section. An assumption which is inherent to many investigations of two dimensional contractions of the LV.

The second assumption is that on a longitudinal cross section, the corresponding radius of curvature at any location is very large with respect to the instantaneous strain involved so that it might be taken for a very short interval of time as constant (the radius of curvature, however, varies from one location to the other).

The LV muscle is divided into many (up to 120) small myocardial elements. Each element is represented by two radius of curvature $R\theta\theta$, $R\phi\phi$ and wall thickness W. The element is assumed to consist of 10 layers of fibers, where all sarcomeres in each layer are parallel to each other and have the length and the same angle of inclination from the horizontal plane.

The points obtained trace the endocardial and epicardial contours and can have points interpolated according to Akima (see Akima, H., "A New Method of Interpolation and Smooth Curve Fitting Based on Local Procedures," Journal of the Assn. for Computing Machinery, Vol. 17, pp. 589-602, Oct. 1970) yielding segmentally or helically plotted cage model 15. Of course other methods well known in the art, such as spline fitting, can be used as well.

This technique as described by AKIMA is as follows: "The method is based on a piecewise function composed of a set of polynomials, each of degree three, at most, and applicable to successive intervals of the given points.

We assume that the slope of the curve at each given point is determined locally by the coordinates of five points, with the point in question as a center point, and two points on each side of it.

A polynomial of degree three representing a portion of the curve between a pair of given points is determined by the coordinates of and the slopes at the two points.

Since the slope of the curve must thus be determined also at the end points of the curve, estimation of two more points is necessary at each end point.

Slope of the Curve

With five data points 1, 2, 3, 4, and 5 given in a plane, we seek a reasonable condition for determining the slope of the curve at point 3. It seems appropriate to assume that the slope of the curve at point 3 should approach that of line segment 23 when the slope of 12 approaches that of 23. It is also highly desirable that the condition be invariant under a linear-scale transformation of the coordinate system. With these rather intuitive reasonings as a guideline, the condition of determining the slope is still not unique.

We assume that the slope t of the curve at point 3 is determined by $$t = (|m_4 - m_3|m_2 + |m_2 - m_1|m_3)/(|m_4 - m_3| + |m_2 - m_1|) \quad (1)$$

where $m_1$, $m_2$, $m_3$, and $m_4$ are the slopes of line segments 12, 23, 34, and 45, respectively. Under this condition, the slope t of the curve at point 3 depends only on the slopes of the four line segments and is independent of the interval widths. Under condition (1), $t = m_2 n$ when $m_1 = m_2$ and $m_3 \neq m_4$, and $t = m_3$ when $m_3 = m_4$ and $m_1 \neq m_2$, as desired. It also follows from (1) that, when $m_2 = m_3$, $t = m_2 = m_3$. Invariance of condition (1) under a linear scale transformation of the coordinate system is also obvious.

A New Method of Interpolation and Smooth Curve Fitting

When $m_1 = m_2 \neq m_3 = m_4$, the slope t is undefined under condition (1): the slope t can take any value between $m_2$ and $m_3$ when $m_1$ approaches $m_2$ and $m_4$ approaches $m_3$ simultaneously. It is a cornerstone of our new method that $t = m_2$ and, similarly, $t = m_3$ when $m_4 = m_3$, and these two rules conflict when $m_1 = m_2 \neq m_3 = m_4$; therefore, no desired curve exists under condition (1) in this special case. (In order to give a definite unique result in all cases, the slope t is equated to $\frac{1}{2}(m_2 + m_4)$ as a convention for this case in the computer programs. This convention is also invariant under a linear scale transformation of the coordinate system.)

Interpolation Between A Pair of Points

We try to express a portion of the curve between a pair of consecutive data points in such a way that the curve will pass through the two points and will have at the two points the slopes determined by the procedure described. To do so, we shall use a polynomial because "polynomials are simple in form, can be calculated by elementary operations, are free from singular points, are unrestricted as to range of values, may be differentiated or integrated without difficulty, and the coefficients to be determined enter linearly." Since we have four conditions for determining the polynomial for an interval between two points $(x_1, y_1)$ and $(x_2, y_2)$, i.e.

$$y = y_1 \text{ and } \frac{dy}{dx} = t_1 \text{ at } x = x_1.$$

$$y = y_2 \text{ and } \frac{dy}{dx} = t_2 \text{ at } x = x_2.$$

where $t_1$ and $t_2$ are the slopes at the two points, a third-degree polynomial can be uniquely determined. Therefore, we assume that the curve between a pair of points can be expressed by a polynomial of, at most, degree three.

The polynomial, though uniquely determined, can be written in several ways. As an example we shall give the following form:

$$y = p_0 + p_1(x-x_1) + p_2(x-x_1)^2 + p_3(x-x_1)^3 \quad (2)$$

where $$p_0 = y_1 \quad (3)$$

$$p_0 = t_1 \quad (4)$$

$$p_2 = [3(y_2-y_1)/(x_2-x_1) - 2t_1 - t_2]/(x_2-x_1) \quad (5)$$

$$p_3 = [t_1 + t_2 - 2(y_2-y_1)/(x_2-x_1)]/(x_2-x_1)^2 \quad (6)$$

Estimation of Two More Points at an End Point

At each end of the curve, two more points have to be estimated from the given points. We assume for this purpose that the end point $(x_3, y_2)$ and two adjacent given points $(x_2, y_2)$ and $(x_1, y_1)$, together with two more points $(x_4, y_4)$ and $(x_5, y_{15})$, to be estimated, lie on a curve expressed by $$y = g_0 + g_1(x-x_3) + g_2(x-x_3)^2 \quad (7)$$

where the g's are constants. Assuming that $$x_6 - x_3 = x_4 - x_2 = x_2 - x_1 \quad (8)$$

we can determine the ordinates $y_4$ and $y_6$, corresponding to $x_4$ and $x_6$, respectively, from (7). The results are $$\begin{aligned}(y_5 - y_4)/(x_5 - x_4) &- (y_4 - y_3)/(x_4 - x_3) \\ = (y_4 - y_3)/(x_4 - x_2) &- (y_3 - y_2)/(x_3 - x_2) \\ = (y_3 - y_2)/(x_3 - x_2) &- (y_2 - y_1)/(x_2 - x_1).\end{aligned} \quad (9)$$

The helical shape itself is described in Azhari H., Sideman S., Beyar R., Grenadier E., Dinnar U.: *An analytical shape descriptor of 3-D geometry. Application to the analysis of the left ventricle shape and contraction.* IEEE Trans. on Biomed Eng. 34(5): 345-355, 1987. This approach is summarized as follows: "Helical Coordinate Approximation Assume that the LV is surrounded by a cylinder of diameter D where D is larger than the lateral diameter of the LV and its axis parallel to the long axis of the LV (FIG. 1). By moving along the helical coordinate $\xi$ on the surface of the cylinder and measuring the distance from the cylinder wall to the LV wall along the vector R (which points inwards to the cylinder's axis of symmetry) one obtains a unidimensional function of $R = R(\xi)$. The 3-D shape of the LV can thus be reconstructed from this function in cylindrical coordinates $(Z, r, \theta)$, using the following set of equations.

$$Z = (\xi/Lo)Ho \quad (1a)$$

$$3DS = r = D/2 - R(\xi) \quad (1b)$$

$$\theta = 2\pi[\xi/Lo - \text{INTEGER }(\xi/Lo)] \quad (1c)$$

where
3DS = the 3-D shape
Ho = height of one helical step
D = diameter of the cylinder
Lo = length of one coil, given by $[H_0^2 + (\pi D)^2]^{\frac{1}{2}}$
Z = vertical coordinate
r = radial position of the surface
$\theta$ = angular coordinate.

A Fourier series expansion can now be employed to approximate the function $R(\xi)$ which contains information over the range $0 \leq \xi \leq L$ where L equals the integrated path length along the $\xi$ coordinate, measured from apex to base. However, in order to obtain a more convenient representation, an antisymmetric image is first added to the actual data yielding the expanded function $f(\xi)$. This is defined by $$f(\xi) = \begin{cases} R(\xi) - D/2; & 0 \leq \xi \leq L \\ D/2 - R(2L - \xi); & L < \xi \leq 2L. \end{cases} \quad (2)$$

Next, the Fourier series expansion for $f(\xi)$ is taken over the range 2L. By so doing the Fourier series assumes the form of a sine series (since all the cosine coefficients are equaled to zero) and the dc variable Ao will always be equal to D/2. Thus, the analytical expression obtained for $R(\xi)$ is given by $$R(\xi) = D/2 + \sum_{n=1}^{N} An \text{SIN}(n\pi\xi/L) \quad (3)$$

where
N = number of harmonics taken for the derived approximation
An = Fourier constant of order n.

It is noted that the method is applicable to any closed 3-D surface for which every vector along $\xi$ is uniquely defined, i.e., there are no "pockets" within the shape.

Spectral Representation

The fourier sine series expansion may readily serve as a tool for the spectral analysis of the 3-D data. Alternatively, a discrete Fourier transform of the unexpanded data may be utilized so as to avoid effects of the data expansion.

In order to eliminate the effects of the geometrical size and provide a comparable data representation, the spectral information of each LV is normalized using the following equations.

$$Sa(n) = |An| / \sum_{n=1}^{N} |An| \quad (4a)$$

$$Sv(n) = An^2 / \sum_{n=1}^{N} An^2 \quad (4b)$$

where
Sa(n) = relative amplitude of harmonic n

Sv(n) = relative squared amplitude (power) of harmonic n.

The computer algorithm for generating the helical shape from CT is described in Azhari, Grenadier, Dinnar, Beyar, Adam, Marcus and Sideman, op cit.

The latter is subjected to shading and coloring by a video input represented at 16 to apply shading and coloring to the various portions of the heart display so as to enable subsequently applied colorings representing a variety of stress and pathological conditions to be readily distinguishable.

To the computer model thus produced, regional color representing stress and dysfunction conditions can be applied at 17 in a second stage represented generally at II.

Using the techniques described in the aforementioned publications, we can provide a stress and function analysis at 18 which compares the results following edge detection with stored three-dimensional images or data representing stored conditions at 19 with the actual measurement of thickening and the like (see the Beyar, Shapiro, Rogers, Solen, Weiss, Weisfeldt article cited earlier) to provide the regional color modification of the model representing stress and dysfunction. In stage III as represented at block 20, a video display can be provided with regional deformations 21, shown in contrasting color from the color of remaining regions 22 of the color model 23. An animation input at 24 to the video display can apply the beating action of the heart.

In a fourth important IV step of the invention, an angiogram of the same patient is taken as represented at 25, either contemporaneously with the two-dimensional sections or prior to or subsequent to such sections and the angiogram data is stored.

From the angiogram, the coronary artery architecture or structure is generated at 26. We start with angiograms to determine individual characteristics and locations and degree of lesions; we then reconstruct the coronary tree by utilizing anatomical landmarks; we evaluate blood supply for each region by one or more mathematical models and compare to local mechanical dysfunction(s); we evaluate regions of normal and abnormal blood flow and mechanical dysfunction.

Utilizing a characteristic structural element on the model 23 for positioning the arterial tree, the arteries are superimposed thereon at 27 and as represented at V, in the video display 28, the colored heart 29 is depicted with colored regions 30, 31 and 32 representing stress areas, infarcts, wall thickenings or other myocardial pathologies. The coronary tree 33 is likewise displayed thereon. An input at 34 can serve to provide color animation in real time and can provide rotation as may be required to allow all sides of the heart to be viewed.

Contemporaneously, from the reconstructed arterial tree, we can analyze the latter at 35 to determine the effect of regional pathology or mechanical dysfunction and can compare these effects with simulated and real effects on mechanical behavior at 36. The effects of physical and pharmaceutical intervention can be simulated by inputs at 37 as previously described, for example, to increase contractile force, or to decrease contractile force. The effects of more rapid or slower heart beats can be introduced at this point to determine the apparent and real effect on the beating heart. The analysis may include suggested diagnosis and intervention as represented at 38.

We can, for example, simulate regional ischemia by the application of flow thickening relationships as a means of varying the normal three-dimensional heart shape as described in Azhari H., Sideman S., Shapiro E., Weiss J., Graves W., Rogers W., Weisfeldt M., Beyar R.,: 3-D mapping by acute ischemic regions by wall thickening as compared to wall motion analysis form magnetic resonance images (submitted to Circulation, 1989).

It will thus be apparent that the display not only can be used diagnostically with great effect, since it can allow the relationship of actual structures of the arterial tree and malfunctions thereof to be correlated with clearly visible dysfunction in the animated heart and the locations of stress, infarct or pathology in the myocardium, but it also has value as an educational and research tool.

The 3-D motion-based analysis of cardiac function is effected by the method described in Azhari H., Beyar R., Sideman S.: A comparative study of three-dimensional left ventricular wall motion in acute ischemia using a canine model. Analysis and Simulation of the Cardiac System: Inhomogeneity and Imaging, Sideman S., and Beyar R., Editors, Freund Publishers, London, 1989 (in press).

We claim:

1. A method of displaying the coronary anatomy, superimposed on and complementing a 3D shape and function of a mammalian heart, comprising the steps of:
   (a) electronically generating a plurality of two-dimensional sections of a mammalian heart;
   (b) subjecting said sections automatically to a segmental or helical pattern analysis to generate a three-dimensional model of said mammalian heart;
   (c) subjecting said mammalian heart to angiography to obtain a picture of the coronary artery pattern of said mammalian heart;
   (d) superimposing said coronary artery pattern on said three-dimensional model using as a reference for locating said coronary artery pattern relative to said model a structural element of said mammalian heart detected in said model; and
   (e) displaying said model with said artery pattern superimposed thereon in a three-dimensional display.

2. The method defined in claim 1 wherein said plurality of two-dimensional sections of a mammalian heart are electronically generated in step (a) by MRI.

3. The method defined in claim 1 wherein said plurality of two-dimensional sections are obtained by ultrasound imaging of said mammalian heart.

4. The method defined in claim 1 wherein said plurality of two-dimensional sections of a mammalian heart are generated in step (a) by computer tomography.

5. The method defined in claim 1, further comprising the step of subjecting the displayed model with said artery pattern superimposed thereon to animation representing a beating of the heart represented by said model.

6. The method defined in claim 5 wherein the stored three-dimensional models include models of hearts with coronary diseases including ischemic heart disease and infarcts, aneurysm, hypertrophy, cardiomyopathy and valvular diseases.

7. The method defined in claim 1, further comprising the step of storing three-dimensional models or data in analytical or compressed form representing a normal heart and hearts with various pathologies, electronically comparing said displayed model with the stored three-dimensional models or said data, and automatically indicating a pathological state of said mammalian heart by the comparison.

8. The method defined in claim 1, further comprising the steps of analyzing said sections for ascertaining a regional physiological stress representing regional loading, and differently coloring regions of said model with different regional physiological stress.

9. The method defined in claim 1, further comprising the steps of analyzing said sections for ascertaining regional geometric characteristics representing mechanical degradation at certain zones of said mammalian heart, and differently coloring regions of said model with different mechanical degradations.

10. A method of displaying the function of a mammalian heart, comprising the steps of:
  (a) generating a plurality of two-dimensional sections of a mammalian heart;
  (b) subjecting said sections automatically to a segmental or helical pattern analysis to generate a three-dimensional model of said mammalian heart;
  (c) analyzing said sections for ascertaining a presence of mechanical degradation of certain zones of the heart;
  (d) electronically coloring zones of the displayed model corresponding to said certain regions;
  (e) displaying said model with said colored zones; and
  (f) subjecting the model displayed in step (e) to video animation.

11. The method defined in claim 10 wherein said plurality of two-dimensional sections of a mammalian heart are electronically generated in step (a) by MRI.

12. The method defined in claim 10 wherein said two-dimensional sections are obtained by ultrasound imaging of the mammalian heart.

13. The method defined in claim 10 wherein said plurality of two-dimensional sections of a mammalian heart are electronically generated in step (a) by computer tomography.

14. The method defined in claim 10 wherein the displayed model with said artery pattern superimposed thereon is subjected to animation representing a beating of the heart represented by said model.

15. The method defined in claim 10, further comprising the step of storing three-dimensional models representing characteristic normal hearts and hearts with various pathologies, electronically comparing said displayed model with the stored three-dimensional models, and automatically indicating a pathological state of said mammalian heart by the comparison.

16. The method defined in claim 15 wherein the stored three-dimensional models include models of hearts with coronary diseases including stenosis, ischemic heart disease and infarct, aneurysm, hypertrophy, cardiomyopathy and valvular diseases.

17. The method defined in claim 1, further comprising the steps of subjecting the heart displayed in step (e) to animation and analyzing simulated and real effects on the mechanical behavior of the animated heart.

* * * * *